(12) United States Patent
Moore et al.

(10) Patent No.: US 7,231,258 B2
(45) Date of Patent: Jun. 12, 2007

(54) COMMUNICATING MEDICAL EVENT INFORMATION

(75) Inventors: Mark P. Moore, Redmond, WA (US); Ward A. Silver, Vashon, WA (US)

(73) Assignee: MedTronic Physio-Control Corp., Redmond, WA (US)

( * ) Notice: Subject to any disclaimer, the term of this patent is extended or adjusted under 35 U.S.C. 154(b) by 467 days.

(21) Appl. No.: 10/330,808

(22) Filed: Dec. 26, 2002

(65) Prior Publication Data

US 2004/0127774 A1 Jul. 1, 2004

(51) Int. Cl.
*A61N 1/36* (2006.01)

(52) U.S. Cl. .......................... 607/60; 607/32; 128/903

(58) Field of Classification Search ................. 607/2, 607/4–5, 32, 60; 128/903–904
See application file for complete search history.

(56) References Cited

U.S. PATENT DOCUMENTS

| | | | |
|---|---|---|---|
| 4,635,639 A | 1/1987 | Hakala et al. | |
| 5,507,782 A * | 4/1996 | Kieval et al. .................. 607/9 |
| 5,549,115 A | 8/1996 | Morgan et al. | |
| 5,549,659 A | 8/1996 | Johansen et al. | |
| 5,593,426 A | 1/1997 | Morgan et al. | |
| 5,674,252 A | 10/1997 | Morgan et al. | |
| 5,680,864 A | 10/1997 | Morgan et al. | |
| 5,683,423 A | 11/1997 | Post | |
| 5,749,902 A | 5/1998 | Olson et al. | |
| 5,749,913 A | 5/1998 | Cole | |
| 5,782,878 A | 7/1998 | Morgan et al. ................ 607/5 |
| 5,787,155 A | 7/1998 | Luna | |
| 5,836,993 A | 11/1998 | Cole | |
| 5,891,046 A | 4/1999 | Cyrus et al. | |
| 5,891,049 A | 4/1999 | Cyrus et al. | |
| 5,899,866 A | 5/1999 | Cyrus et al. | |
| 5,921,938 A | 7/1999 | Aoyama et al. | |
| 5,951,485 A | 9/1999 | Cyrus et al. | |
| 5,999,493 A | 12/1999 | Olson | |
| 6,041,257 A | 3/2000 | MacDuff et al. | |
| 6,047,207 A | 4/2000 | MacDuff et al. | |

(Continued)

FOREIGN PATENT DOCUMENTS

WO WO 02/060529 A2 8/2002

OTHER PUBLICATIONS

"Heartstream FR2 Semi Automatic External Defibrillator (AED)," 5 pages, http://www.shopmash.com/mash_heartstrean_info.htm.

(Continued)

*Primary Examiner*—Carl Layno

(57) ABSTRACT

In general, the invention provides techniques for wireless communication of medical event information between medical devices that treat a particular patient. In general, medical event information describes the condition and treatment of a patient. A medical device may detect another medical device via a wireless communications medium, and establish a local wireless communication session the other device in order to receive medical event information stored by the other device for a patient. The wireless communications medium may be a radio frequency communications medium, and the medical devices may establish a local wireless communication session according to any of a number of local wireless data communication standards. The medical event information received from the other medical device may be used to select a therapy, or to generate a report or patient chart detailing the condition and treatment of the patient.

35 Claims, 6 Drawing Sheets

U.S. PATENT DOCUMENTS

| | | |
|---|---|---|
| 6,057,758 A | 5/2000 | Dempsey et al. |
| 6,141,584 A | 10/2000 | Rockwell et al. ............... 607/5 |
| 6,141,588 A * | 10/2000 | Cox et al. ...................... 607/9 |
| 6,150,951 A | 11/2000 | Olejniczak |
| 6,201,992 B1 | 3/2001 | Freeman |
| 6,301,502 B1 | 10/2001 | Owen et al. |
| 6,304,780 B1 | 10/2001 | Owen et al. |
| 6,321,113 B1 * | 11/2001 | Parker et al. .................. 607/5 |
| 6,374,138 B1 | 4/2002 | Owen et al. |
| 6,405,083 B1 | 6/2002 | Rockwell et al. |
| 6,427,083 B1 | 7/2002 | Owen et al. |
| 6,438,417 B1 | 8/2002 | Rockwell et al. |
| 6,493,581 B2 * | 12/2002 | Russell ........................ 607/5 |
| 6,574,511 B2 * | 6/2003 | Lee ............................... 607/60 |
| 6,594,634 B1 | 7/2003 | Hampton et al. |
| 6,597,948 B1 | 7/2003 | Rockwell et al. |
| 6,668,192 B1 | 12/2003 | Parker et al. |
| 6,675,044 B2 * | 1/2004 | Chen ........................... 607/30 |
| 2002/0123778 A1 | 9/2002 | Linberg |
| 2002/0169584 A1 | 11/2002 | Fu et al. |
| 2002/0193846 A1 * | 12/2002 | Pool et al. .................... 607/60 |
| 2003/0025602 A1 | 2/2003 | Medema et al. |
| 2003/0058097 A1 | 3/2003 | Saltzstein et al. |
| 2003/0109904 A1 | 6/2003 | Silver et al. |
| 2003/0149526 A1 * | 8/2003 | Zhou et al. .................. 701/213 |
| 2004/0088027 A1 * | 5/2004 | Burnes et al. ................ 607/60 |

OTHER PUBLICATIONS

"ZOLL Software Information," 6 pages, http://www.pinpointtech.com/zolldata/.

"Medium Access Control (MAC) and Physical (PHY) Specifications," ANSI/IEEE Std 802.11, 1999 Edition.

* cited by examiner

US 7,231,258 B2

COMMUNICATING MEDICAL EVENT INFORMATION

TECHNICAL FIELD

The invention relates medical devices, and more particularly, to medical device communication.

BACKGROUND

A defibrillator is a device that stores energy, typically in one or more high-voltage capacitors, and delivers the stored energy to a patient. In particular, a defibrillator delivers energy to a heart that is undergoing ventricular fibrillation and has lost its ability to contract. Ventricular fibrillation is particularly life threatening because activity within the ventricles of the heart is so uncoordinated that virtually no pumping of blood takes place. If untreated, the patient whose heart is undergoing fibrillation may die within a matter of minutes.

An electrical pulse delivered to a fibrillating heart may depolarize the heart and cause it to reestablish a normal sinus rhythm. An external defibrillator applies a defibrillation pulse via electrodes placed upon the chest of the patient. When a switch is closed, the defibrillator delivers at least some of the stored energy to the patient. In some cases, the patient may need multiple shocks, and different quantities of energy may be delivered with each shock.

The defibrillator may also monitor the patient via the electrodes, and generate a record of the condition and treatment of the patient. For example, the defibrillator may record an electrocardiogram (ECG) of the patient sensed via the electrodes. The defibrillator may keep track of the therapy provided to the patient by recording the types and energy levels of defibrillation pulses delivered to the patient and the time at which these pulses were delivered. The defibrillator may also include a microphone to make an audio recording of the treatment of the patient. These and other types of information surrounding the treatment of the patient, i.e., medical event information, may be stored within a memory of the defibrillator.

In some cases, the patient may be treated with more than one medical device. For example, the patient may have initially received prompt defibrillation therapy with an automatic external defibrillator (AED). In order to provide therapy as quickly as possible, many public and non-public venues, as well as first responders, such as police and fire personnel, are equipped with AEDs. An AED is designed to allow minimally trained operators to use the AED to deliver prompt therapy. AEDs differ from manual defibrillators in that AEDs can automatically analyze the ECG of the patient to determine whether defibrillation is necessary, and can automatically select energy levels for defibrillation pulses from preprogrammed progressions of energy levels. In most AED designs, the first responder is prompted to press a button when the AED determines that defibrillation is warranted and is ready to deliver a defibrillation pulse.

Typically, Advanced Cardiac Life Support (ACLS) trained emergency medical personnel, e.g. paramedics, arrive shortly thereafter to take over the treatment of the patient with a second defibrillator, which is usually more fully featured than an AED. The paramedics may need to use the second defibrillator to treat the patient. When the patient arrives at the emergency department of a hospital, the patient may be treated with a third defibrillator located therein. Each defibrillator used to treat the patient will store medical event information concerning the treatment.

SUMMARY

In general, the invention provides techniques for wireless communication of medical event information between medical devices that treat a particular patient. A medical device may detect another medical device via a wireless communications medium, and establish a local wireless communication session with the other device in order to receive medical event information stored by the other device. The wireless communications medium may be a radio frequency communications medium, and the medical devices may establish a local wireless communication session according to any of a number of local wireless data communication standards.

In an exemplary application, a patient is initially treated with an AED. The AED generates medical event information relating to the condition and treatment of the patient, and stores the medical event information in a memory. Later, when paramedics arrive, a second defibrillator detects the presence of the AED and establishes a local wireless communication session with the AED in order to receive the medical event information stored in the AED. The second defibrillator may coordinate the delivery of therapy to the patient with the AED, and may select a therapy to deliver to the patient based on the received medical event information. For example, the second defibrillator may select a defibrillation pulse energy level for a defibrillation pulse to be delivered to the patient based on the energy levels of unsuccessful defibrillation pulses already delivered to the patient by the AED as indicated in the medical event information received from the AED.

The caregivers that treat the patient with the AED and the second defibrillator may be required to generate "run reports" detailing the condition and treatment of the patient. The caregivers may use computers to generate run reports. The computers may detect and establish a local wireless communication session with one or both of the defibrillators to receive the medical event information stored therein to assist in the generation of run reports.

If the patient is later taken to a hospital by the paramedics, a defibrillator and/or a computer in the hospital may detect and establish a local wireless communication session with the second defibrillator or the computer used by the paramedics in order to receive the medical event information stored therein. The defibrillator at the hospital may use the medical event information to select a therapy, or the computer at the hospital may distribute the medical event information to caregivers at the hospital and generate a patient chart using the medical event information.

In one embodiment, the invention is directed to a method in which a device is detected via a wireless communication medium. Whether the detected device is a medical device and is associated with a patient is determined, and a local wireless communication session is established with the device based on the determination. Medical event information is received from the detected device. The detected device may be an external defibrillator.

In another embodiment, the invention is directed to a device that includes a transceiver to transmit and receive signals via a wireless medium. The device also includes a processor. The processor detects another device via the transceiver and the wireless medium. The processor further determines whether the detected device is a medical device and is associated with a patient, and establishes a wireless communication session with the detected device based on the determination. The processor also receives medical event information from the detected device. The detected device may be an external defibrillator.

In another embodiment, the invention is directed to a computer-readable medium containing instructions. The instructions cause a programmable processor to detect a device via a wireless medium. The instructions further cause a programmable processor to determine whether the detected device is a medical device and is associated with a patient, and establish a local wireless communication session with the detected device based on the determination. The instructions further cause a programmable processor to receive medical event information from the detected device.

In another embodiment, the invention is directed to a method in which medical event information is received from a first medical device via a second medical device and a local wireless communication session between the first medical device and the second medical device. A therapy to deliver to a patient is selected based on the medical event information via the second medical device, and the selected therapy is delivered to the patient via the second medical device. The first and second device may comprise external defibrillators.

In another embodiment, the invention is directed to a device. The device includes a transceiver to provide a local wireless communication system with a medical device, and a circuit coupled to a patient. The device also includes a processor that receives medical event information from the medical device via the local wireless communication channel and the transceiver, select a therapy to deliver to a patient based on the medical event information, and deliver the therapy to the patient via the circuit. The medical device may be an external defibrillator.

In another embodiment, the invention is directed to a computer-readable medium containing instructions. The instructions cause a programmable processor to receive medical event information from a medical device via a local wireless communication session with the medical device, select a therapy to deliver to a patient based on the medical event information, and deliver the selected therapy to the patient.

The invention can provide one or more advantages. For example, wireless communication of medical event information between multiple medical devices associated with the treatment of a patient may allow a medical device that receives medical event information from another medical device to have a more complete description of the condition and treatment of the patient. The medical event information stored within previous defibrillators may be used by subsequent caregivers to provide more effective, e.g., non-redundant, therapy. Further, the medical event information stored in previous defibrillators may be used to generate a more complete patient record at the hospital, and by the prior caregivers to more easily generate more complete "run reports." As the patient is transferred from caregiver to caregiver, medical event information generated by devices that no longer accompany the patient may be transferred from device to device with the patient, allowing, for example, a more complete record of the condition and treatment of the patient in the field to be available to caregivers at a hospital. In this manner, the invention may promote continuity of treatment between two or more devices applied to the patient at different times.

A medical device may advantageously avoid wireless communication with a non-medical device by first determining whether detected devices are medical devices. Moreover, a medical device may receive relevant medical event information by determining which of a plurality of detected medical devices is associated with the patient. Determining whether a detected device is associated with the patient may be particularly advantageous in situations where multiple medical device are present for the treatment of multiple patients, such as the scene of a multiple vehicle accident, or within a hospital emergency department.

The wireless exchange of medical event information between medical devices according to the invention may be hands-free. Medical devices need not be tethered to each other by data cables that could restrict the free movement of caregivers. Further, medical event information may be exchanged without the use of data cards, which may be lost or mishandled losing data, and once given away are unavailable for the generation of a run report or patient chart. The medical devices need not be adjacent to each other, or have a line of sight between each other in order to exchange medical event information.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
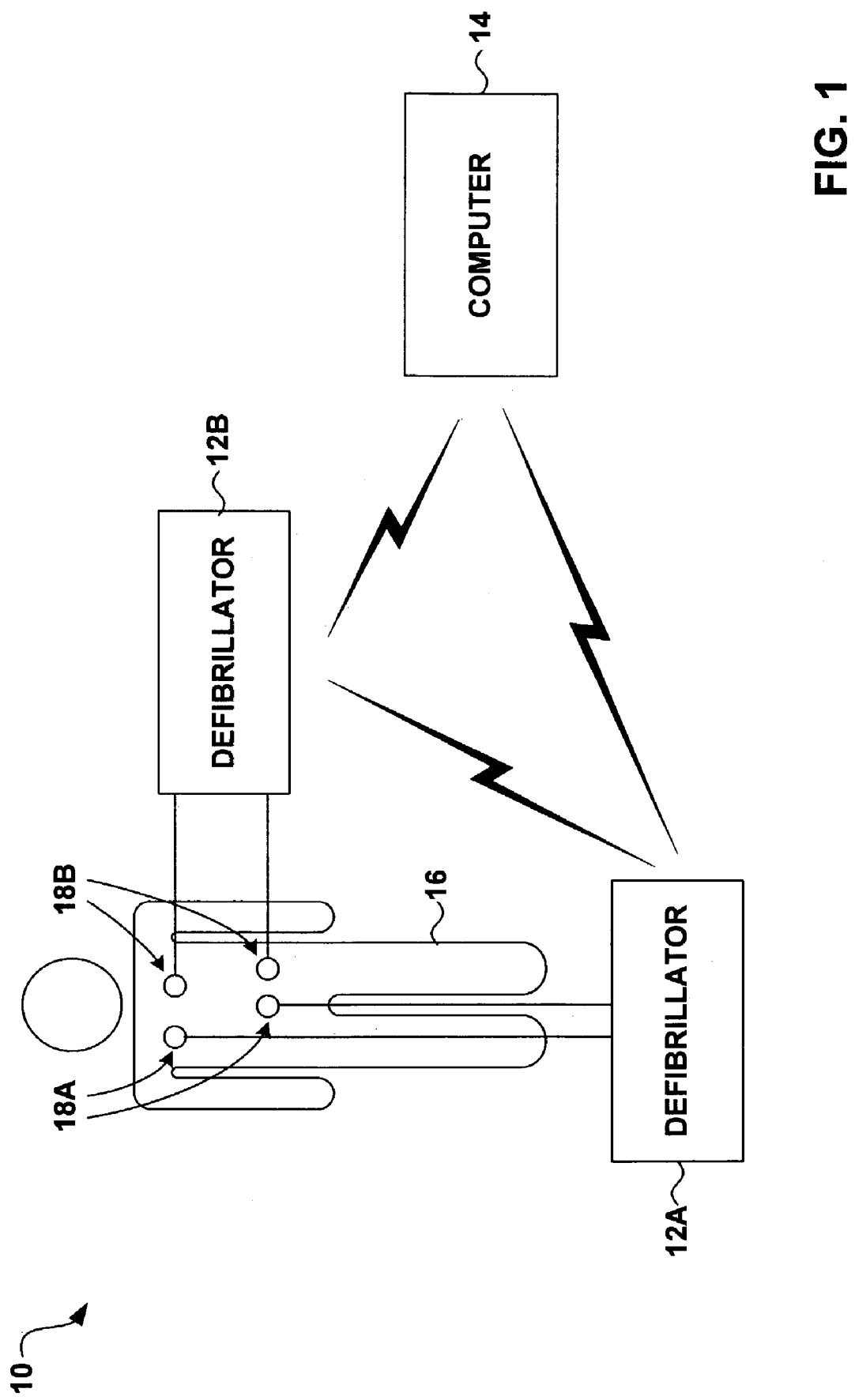
FIG. 1 is a block diagram illustrating an example environment in which medical event information may be wirelessly communicated between medical devices according to an embodiment of the invention.

FIG. 1 is a block diagram illustrating an example environment 10 in which medical event information may be wirelessly communicated between medical devices, such as external defibrillators 12A and 12B, and computer 14. Each of defibrillators 12A and 12B may be associated with a different caregiver present to treat a patient 16. Computer 14 may also be associated with one of the caregivers.

For example, if patient 16 collapses due to ventricular fibrillation, a first responder, such as a police officer, fireman, security guard, or the like, may be the first to arrive on the scene with defibrillator 12A. Defibrillator 12A may be an automatic external defibrillator (AED). The first responder attaches electrode set 18A of defibrillator 12A to the chest of patient 16.

Defibrillator 12A senses electrical activity of the heart of patient 16 via electrode set 18A, and determines whether patient 16 exhibits a shockable rhythm based on the sensed electrical activity. If patient 16 exhibits a shockable rhythm, defibrillator 12A may select an energy level for a defibrillation pulse, charge an energy storage circuit to the selected energy level, and prompt the first responder to deliver the defibrillation pulse upon the storage circuit reaching the selected energy level. The first responder may push a button to deliver the defibrillation pulse. Alternatively, defibrillator 12A may deliver the pulse automatically after warning the first responder that the pulse will be delivered. Multiple pulses may be delivered at different energy levels within the programmable progression so long as the patient exhibits a shockable rhythm.

Defibrillator 12A stores medical event information concerning the condition and treatment of patient 16 within a memory. For example, defibrillator 12A may store an electrocardiogram (ECG) of patient 16 generated based on the electrical activity sensed via electrode set 18A. Defibrillator 12A may also, for example, store a capnograph of the patient, a plethysmograph of the patient, a heart rate of the patient over time, a pulse rate of the patient over time, a blood oxygen saturation of the patient over time, a blood pressure of the patient over time, end tidal carbon dioxide measurements of the patient, and/or measurements of the fraction of carbon dioxide in air inspired or expired by the patient, each of which may be measured or generated using appropriate sensors and circuitry known in the art. Defibrillator 12A may also store an indication of the times defibrillation pulses were delivered, and a variety of information describing the pulses, e.g., pulse width, amplitude, energy level, whether the pulses where multiphasic, and the like. Defibrillator 12A may include a microphone, and may store an audio recording made during the treatment of patient 16. The audio recording may include verbal notations of the first responder, or conversations between the first responder and another caregiver or patient 16. Defibrillator 12A may begin to record medical event information upon being turned on by the first responder.

One or more paramedics may arrive at the location of patient 16 some time after the first responder, bringing a second external defibrillator 12B. Generally, upon arrival, the paramedics take over the treatment of patient 16. If the condition of patient 16 has not yet stabilized, the paramedics may turn on defibrillator 12B and attach electrodes 18B of defibrillator 12B to patient 16.

Defibrillators 12A and 12B are capable of wireless communication. When both defibrillator 12A and defibrillator 12B are turned on and proximate to each other such that wireless communications is possible, one of defibrillators 12A and 12B may detect the other defibrillator 12A or 12B via a wireless communication medium. Defibrillators 12A and 12B may establish a local wireless communication session in order to communicate medical event information.

Defibrillator 12B need not be coupled to patient 16 in order for defibrillators 12A and 12B to establish the local wireless communication session, so long as each of defibrillators 12A and 12B are within their respective wireless communication range. The range of defibrillators 12A and 12B will depend on the power of transceivers within each of defibrillators 12A and 12B used to facilitate wireless communication, and the conditions of the environment that separates defibrillators 12A and 12B. The invention is not limited to wireless communication from any particular set of locations of defibrillators 12A and 12B. For example, defibrillator 12B may detect defibrillator 12A while defibrillator 12B is located on an ambulance in which the paramedics associated with defibrillator 12B arrived. Further, defibrillators 12A and 12B may wirelessly communicate without a line of sight therebetween and independently of their respective orientations.

The wireless communication medium may be a radio frequency (RF) communication medium, and defibrillators 12A and 12B may establish the local wireless communication session according any of a number of local wireless communication standards. For example, defibrillators 12A and 12B may establish a Bluetooth session according to the Bluetooth specification set, which was promulgated by the Bluetooth Special Interest Group (SIG), and is available for download at http://www.bluetooth.org. As another example, defibrillators 12A and 12B may establish wireless local area networking session such as an IEEE 802.11a session, an IEEE 802.11b session, or an IEEE 802.11g session according to the 802.11 specification set promulgated by the Institute of Electrical and Electronics Engineers (IEEE).

Pre-registration, e.g., prior knowledge of device addresses and capabilities, of defibrillators 12A and 12B with each other may be unnecessary in order to establish a local wireless communication session according to the Bluetooth or 802.11 specification sets. In other words, defibrillators 12A and 12B may be previously unknown to each other, and may establish an ad hoc network according to one of these specification sets. The ability to establish an ad hoc network may allow medical devices, such as defibrillators 12A and 12B, associated with unrelated caregivers to wirelessly communicate medical event information.

Once the communication session is established, defibrillator 12B may receive the medical event information stored in defibrillator 12A, and store the medical event information in a memory of defibrillator 12B. The receipt of medical event information from defibrillator 12A may allow the caregiver associated with defibrillator 12B to provide patient 16 with more effective therapy. For example, defibrillator 12B may use the information concerning the energy level of defibrillation pulses delivered by defibrillator 12A to select an energy level for a next defibrillation pulse to be delivered by defibrillator 12B.

Defibrillator 12B may automatically deliver the pulse at the selected level, display this selection to the paramedics via a user interface, or may simply display the pertinent medical event information to the paramedics and receive an energy level selection made by the paramedics. Receiving the medical event information from defibrillator 12A may allow the paramedics and defibrillator 12B to avoid delivering redundant defibrillation pulse energy levels and pulse types that have already proven to be ineffective, and thus more quickly find an effective energy level and type to reestablish sinus rhythm for the heart of patient 16.

Defibrillator 12B may coordinate the delivery of therapy with defibrillator 12A via the local wireless communication session. For example, defibrillator 12B may deliver a signal to defibrillator 12A indicating that the defibrillator 12B is "taking over" the treatment of patient 16 and that defibrillator 12A should suspend the delivery of therapy via defibrillator 12A. In response to such a signal, defibrillator 12A may, for example, stop automatically delivering defibrillation pulses from a preprogrammed progression.

In addition to the medical event information received from defibrillator 12A, defibrillator 12B may generate additional medical event information related to treatment provided to patient 16 by the caregivers associated with defibrillator 12B, and store this newly generated medical event information in the memory of defibrillator 12B with the medical event information received from defibrillator 12A. The medical event information generated by defibrillator 12B may also include items such as an ECG, a capnograph of the patient, a plethysmograph of the patient, a heart rate of the patient over time, a pulse rate of the patient over time, a blood oxygen saturation of the patient over time, a blood pressure of the patient over time, end tidal carbon dioxide measurements of the patient, measurements of the fraction of carbon dioxide in air inspired or expired by the patient, information describing defibrillation pulses delivered by defibrillation 12B, and an audio recording as described above.

As mentioned above, defibrillator 12B may be associated with paramedics and may be more fully featured than defibrillator 12A. Defibrillator 12B may, for example, include multiple electrodes (not shown) in addition to electrode set 18B used to sense electrical activity within the heart of patient 16 and generate an ECG. Defibrillator 12B may also include additional sensors, such as sensors to measure blood oxygen saturation, blood pressure, or respiration, and may store the signals generated by these sensor as medical event information. Either of defibrillators 12A and 12B may allow their respective caregivers to mark the time of the occurrence of various events, such as the delivery of drugs or the administration of cardiopulmonary resuscitation (CPR), during the treatment of patient 16 by, for example, pressing a key or button at the time when the event occurred. These event markers may also be included within the medical event information sets stored by defibrillators 12A and 12B.

In addition to allowing caregivers to provide patient 16 with more effective therapy, wireless communication of medical event information may allow caregivers to more easily prepare reports detailing the treatment of patient 16, referred to as "run reports." A caregiver associated with either of defibrillators 12A and 12B may generate a run report using computer 14. Paramedics may, for example, be required to generate run reports by a local emergency medical services (EMS) system.

Computer 14 may, for example, be a laptop computer or a handheld computer such as a personal digital assistant (PDA). Computer 14 is capable of wireless communication in the manner described above with reference to defibrillators 12A and 12B. Computer 14 may establish a wireless communication session with one or both of defibrillators 12A and 12B to receive the medical event information stored therein. The wireless communication session may be a Bluetooth session or an 802.11 session as described above, and computer 14 may establish an ad hoc network with one or both of defibrillators 12A and 12B. Computer 14 may store received medical event information in a memory.

For example, computer 14 may be associated with paramedics that use defibrillator. 12B to treat patient 16. Computer 14 may wirelessly receive the medical event information stored by defibrillators 12A and 12B. Computer 14 may establish a wireless communication session with each of defibrillators 12A and 12B in order to receive the medical event information stored within each of defibrillators 12A and 12B, or computer 14 may establish a wireless communication session with defibrillator 12B to receive both the medical event information generated by defibrillator 12B and the medical event information that defibrillator 12B previously received from defibrillator 12A.

Computer 14 may establish a wireless communication session with one or both of defibrillators 12A and 12B at any time and from any location or orientation relative to defibrillators 12A and 12B, so long as the communicating devices are within their respective wireless communication ranges. For example, computer 14 may be carried to patient 16 by the paramedic, or remain located on an ambulance and communicate with one or both of defibrillators 12A and 12B. Computer 14 may also communicate with defibrillator 12B when defibrillator 12B is returned to the ambulance.

The paramedics may use computer 14 and the received medical event information to generate a run report detailing the treatment of patient 16. In some embodiments, computer 14 may automatically generate some or all of the run report based on the received medical event information. Receiving medical event information collected by multiple devices involved in the treatment of patient 16 may allow computer 14 and/or the paramedics to generate a more complete run report detailing a more substantial portion of the treatment of patient 16.

The paramedics may also use computer 14 to store other patient information as medical event information. For example, paramedics may enter demographic information of patient 16, such as name, age, sex, approximate height and weight, or the like, or a description of the condition of patient 16 into computer 14 via a user interface, and this information may be stored within a memory as medical event information. This medical event information may also be useful in the generation of a run report, may be collected at any time, and may be stored with medical event information received from other medical devices, such as defibrillators 12A and 12B. Further, other medical devices, such as defibrillators 12A and 12B may wirelessly receive this medical event information from computer 14 in order to have a more complete set of medical event information.

Although only defibrillators 12A and 12B and computer 14 are illustrated in FIG. 1, any number of medical devices involved in the treatment of patient 16 may wirelessly communicate medical event information according to the invention. For example, caregivers associated with defibrillator 12A may use another computer 14 to wirelessly receive medical event information from one or both of defibrillators 12A and 12B, and generate run reports. Further, each set of caregivers may use multiple computers 14 that wirelessly communicate with defibrillators 12 and/or each other. For example, the paramedics may use a hand-held computer 14 carried to patient 16 to collect patient information and to wirelessly receive other medical event information from defibrillators 12A and 12B. A laptop computer 14 located within an ambulance may later wirelessly receive the medical event information stored in the hand-held computer 14, and be used by the paramedics to generate a run report.

If the paramedics transport patient 16 to a hospital, further wireless communication of medical event information may occur. For example, an additional defibrillator 12 within an emergency department of the hospital may establish a wireless communication session with one or both of defibrillator 12B and computer 14, and receive the medical event information stored therein. The receipt of the medical event information generated during the treatment of patient 16 in the field may allow caregivers at the hospital to provide patient 16 with more effective therapy, as described above.

As another example, another computer 14 at the hospital may establish a wireless communication session with one or both of defibrillator 12B and computer 14, and receive the medical event information stored therein. The hospital computer 14 may also be a hand-held or laptop computer, or may be a desktop computer. An administrator using the hospital computer 14, or the hospital computer 14 itself, may use the medical event information to create a patient chart for patient 16 that includes at least some of the medical event information generated during the treatment of patient 16 in the field. Wireless communication of medical event information in this manner may allow for the more convenient generation of more complete patient records. The hospital computer 14 may be a host on a network, and the medical event information generated during the treatment of patient 16 in the field may be made available on the network to various caregivers throughout the hospital. The availability of the medical event information to caregivers within the hospital may allow the caregivers to provide patient 16 with more effective therapy.

Figure 2:
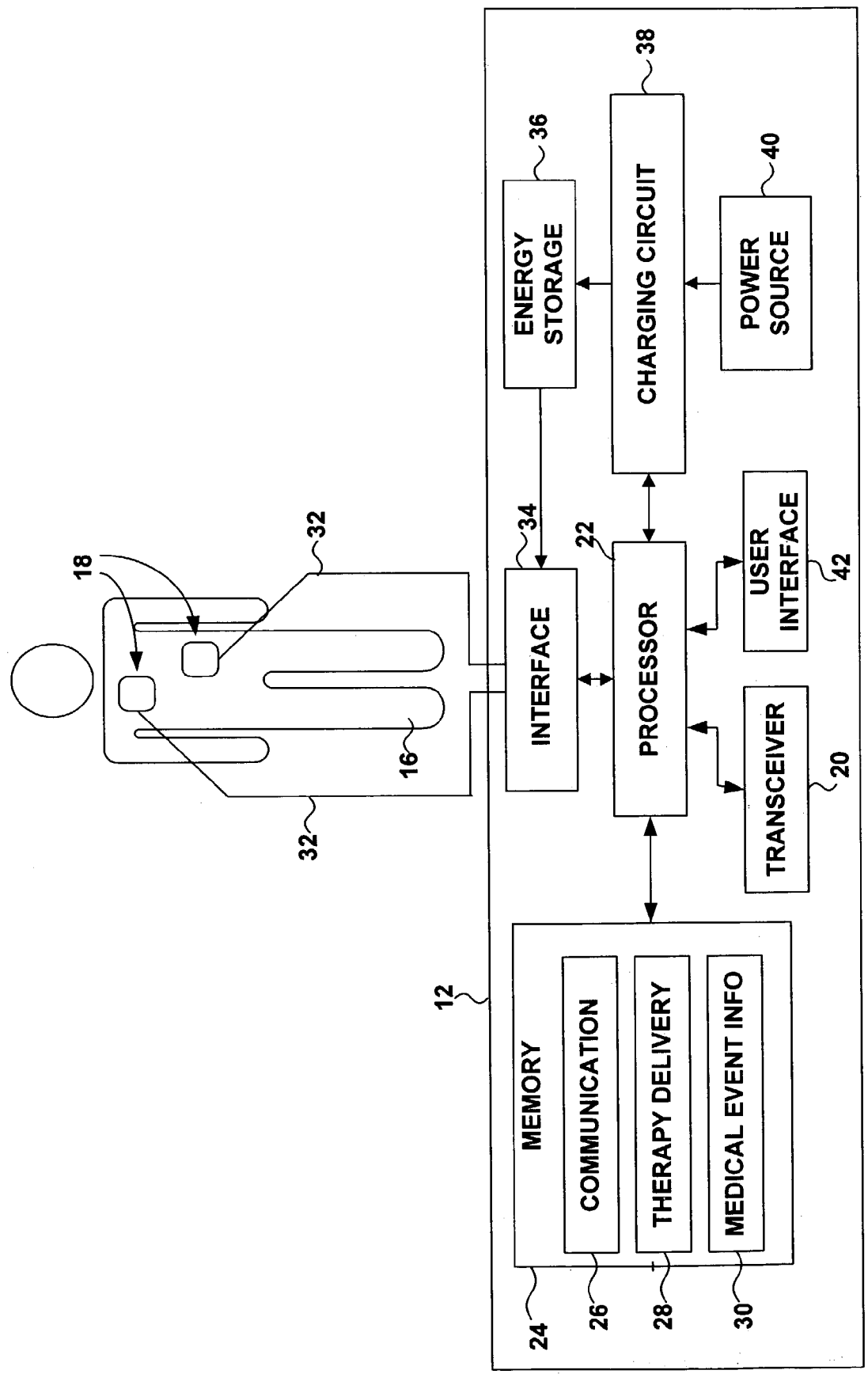
FIG. 2 is a block diagram illustrating components of an example external defibrillator that wirelessly communicates medical event information according to an embodiment of the invention.

FIG. 2 is a block diagram illustrating components of an example external defibrillator 12, such as defibrillators 12A and 12B shown in FIG. 1, that wirelessly communicates medical event information according to an embodiment of the invention. As illustrated in FIG. 2, defibrillator 12 includes a transceiver 20 for wireless communication. Transceiver 20 may include an antenna (not shown) to facilitate wireless communication via a radio frequency communication medium. Transceiver 20 may, for example, take the form of an integrated circuit or PCIMCA card with circuitry configured for wireless communication according, e.g., a wireless network interface card. The wireless network card may be compliant with one or more wireless communication standards such as to one or both of the Bluetooth or 802.11 specification sets A processor 22 coupled to transceiver 20 controls the operation of transceiver 20 to communicate medical event information with other medical devices. Processor 22 also controls the operation of defibrillator 12 to monitor patient 16, provide therapy to patient 16, and generate medical event information during the treatment of patient 16. Processor 22 may, for example, take the form of a microprocessor or an application specific integrated circuit (ASIC).

A memory 24 is accessible by processor 22, and may include program instructions that cause processor 22 to perform the functions attributed to processor 22 herein. Memory 24 may, for example, include communication program instructions 26 that cause processor 22 to wireless communicate medical event information with other medical devices as described herein, and therapy delivery program instructions 28 that cause processor 22 to monitor patient 16, deliver defibrillation pulses to patient 16, and generate medical event information during the treatment of patient 16 as described herein. Memory 24 also includes the medical event information 30 generated during the treatment of patient 16 and/or wirelessly received from other medical devices. Memory 24 may include any of a variety of solid state, magnetic or optical media, such as RAM, ROM, CD-ROM, magnetic disk, or EEPROM.

Although defibrillator 12 is shown coupled to patient 16 in FIG. 2, defibrillator 12 need not be coupled to patient 16 in order to wirelessly communicate medical event information with other medical devices. Rather, defibrillator 12 is coupled to patient 16 in order to facilitate the treatment of patient 16, e.g., sensing electrical activity within the heart of patient 16 and delivering defibrillation pulses to patient 16. Defibrillator 12 is coupled to patient 16 via electrode set 18.

Electrode set 18 may include hand-held electrode paddles or adhesive electrode pads placed on the skin of patient 16. Defibrillator 12 senses the electrical activity of the heart of patient 16 and delivers defibrillation pulses to patient 16 via electrode set 18. Electrode set 18 is coupled to defibrillator 12 via conductors 32 and interface 34. In a typical application, interface 34 includes a receptacle, and connectors 32 plug into the receptacle.

Interface 34 includes a switch (not shown in FIG. 2) that, when activated, couples an energy storage circuit 36 to electrode set 18. Energy storage circuit 36 stores the energy to be delivered to patient 16 in the form of a defibrillation pulse. The switch may be of conventional design and may be formed, for example, of electrically operated relays. Alternatively, the switch may comprise an arrangement of solid-state devices such as silicon-controlled rectifiers or insulated gate bipolar transistors.

Energy storage circuit 36 includes components, such as one or more capacitors, that store the energy to be delivered to patient 16 via electrode set 18. Before a defibrillation pulse may be delivered to patient 16, energy storage circuit 36 must be charged. Processor 22 directs a charging circuit 38 to charge energy storage circuit 36 to a high voltage level. Charging circuit 38 comprises, for example, a flyback charger that transfers energy from a power source 40 to energy storage circuit 36.

As mentioned above, defibrillator 12 may be a manual defibrillator or an AED. Where defibrillator 12 is a manual defibrillator, a caregiver using defibrillator 12 may select an energy level for each defibrillation pulse delivered to patient 12. Processor 22 may receive the selection made by the caregiver via a user interface 42, which may include input devices, such as a keypad and various buttons or dials, and output devices, such as various indicator lights, a CRT, LED, or LCD screen, and a speaker. Where defibrillator 12 is an AED, processor 22 may select an energy level from a preprogrammed progression of energy levels stored in memory 24 based on number of defibrillation pulses already delivered to patient 16.

When the energy stored in energy storage circuit 24 reaches the desired energy level, processor 22 controls user interface 42 to provide an indication to the caregiver that defibrillator 12 is ready to deliver a defibrillation pulse to patient 16, such as an indicator light or a voice prompt. The defibrillation pulse may be delivered manually or automatically. Where the defibrillation pulse is delivered manually, the caregiver may direct processor 22 to deliver the defibrillation pulse via user interface 42 by, for example pressing a button. In either case, processor 22 activates the switch to electrically connect energy storage circuit 36 to electrode set 18, and thereby deliver the defibrillation pulse to patient 16.

Processor 22 may modulate the defibrillation pulse delivered to patient 16. Processor 22 may, for example, control the switch to regulate the shape of the waveform of the pulse and the width of the pulse. Processor 22 may control the switch to modulate the pulse to, for example, provide a multiphasic pulse, such as a biphasic truncated exponential pulse, as is known in the art.

Processor 22 may perform other functions as well, such as monitoring electrical activity of the heart of patient 16 sensed via electrode set 18 and received via interface 34. Processor 22 may determine whether the heart of patient 16 is fibrillating based upon the sensed electrical activity in order to determine whether a defibrillation pulse should be delivered to patient 16. Where a defibrillation pulse has already been delivered, processor 22 may evaluate the efficacy of the delivered defibrillation pulse by determining if the heart is still fibrillating in order to determine whether an additional defibrillation pulse is warranted. Processor 22 may automatically deliver defibrillation pulses based on these determinations, or may advise the caregiver of these determinations via user interface 42. Processor 22 may display an electrocardiogram (ECG) based on the sensed electrical activity via user interface 42.

Processor 22 may store an indication of the time of delivery of each defibrillation pulse delivered to patient 16 as medical event information 30 within memory 24 for patient 16. Processor 22 may also store the energy level of each pulse and other characteristics of each pulse, such as the width, amplitude, or shape, as medical event information 30 for patient 16. Processor may also store a digital representation of the ECG as medical event information 30 for patient 16.

User interface 42 may include a microphone (not shown) that detects sounds in the vicinity of defibrillator 12. Processor 22 may receive signals from the microphone and store an audio recording that includes these signals as medical event information 30 for patient 16. The audio recording may include verbal notations of a caregiver, or conversations between caregivers and patient 16.

The caregiver may mark the time of the occurrence of various events, such as the delivery of drugs or the administration of cardiopulmonary resuscitation (CPR), during the treatment of patient 16 by, for example, pressing a key or button of user interface 42 at the time when the event occurred. These event markers may also be included within medical event information 30 for patient 16. Where defibrillator 12 is more fully featured, e.g., a manual paramedic or hospital defibrillator, defibrillator 12 may also include additional sensors (not shown) coupled to processor 22, such as sensors to measure blood oxygen saturation, blood pressure, or respiration, and processor 22 may store the signals generated by these sensors as medical event information 30 for patient 16.

Processor 22 may establish wireless communication sessions with the other medical devices via transceiver 20 in order to communicate medical event information, as will be described in greater below. Processor 22 may receive medical event information 30 for patient 16 stored in another medical device, such as another defibrillator or a computer 14, and store the received medical event information 30 in memory 24. Processor 22 may also be responsive to requests from other medical devices to provide medical event information 30 for patient 16 stored in memory 24 to the other medical device.

Further, processor 22 may be responsive to instructions received from another medical device, and/or may provide instructions to another medical device in order to coordinate the delivery of therapy to patient 16 with the other medical device. For example, processor 22 may receive a signal from another defibrillator indicating that the other defibrillator is "taking over," i.e., assuming responsibility for, the treatment of patient 16 and that processor 22 should suspend the delivery of therapy via defibrillator 12. In response to such a signal, processor 22 may, for example, disable features of user interface 42 in order to prevent the further delivery of therapy via defibrillator 12, or stop automatically delivering defibrillation pulses from a preprogrammed progression.

Figure 3:
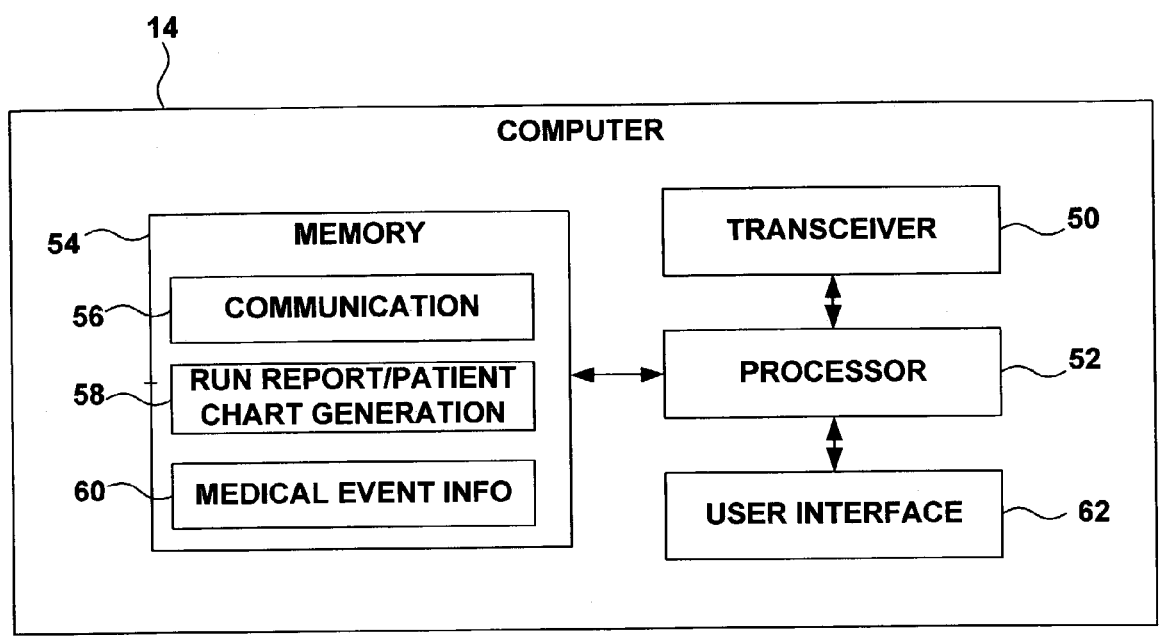
FIG. 3 is a block diagram illustrating components of an example computer that wirelessly communicates medical event information according to an embodiment of the invention.

FIG. 3 is a block diagram illustrating components of an example computer 14 that wirelessly communicates medical event information according to an embodiment of the invention. As mentioned above, computer 14 may, for example, take the form of a laptop computer, hand-held computer, or desktop computer. For example, computer 14 may be a laptop or hand-held computer associated with a first responder or paramedic, or a computer within a hospital.

As illustrated in FIG. 3, computer 14 includes a transceiver 50 for wireless communication. Transceiver 50 may include an antenna (not shown) to facilitate wireless communication via a radio frequency communication medium. Transceiver 50 may, for example, take the form of an integrated circuit or PCIMCA card with circuitry configured for wireless communication according to one or both of the Bluetooth or 802.11 specification sets, e.g., a wireless network interface card.

A processor 52 coupled to transceiver 50 controls the operation of transceiver 50 to exchange medical event information with other medical devices. Processor 52 also controls the operation of computer 14 to generate run reports or patient charts. Processor 52 may, for example, take the form of a microprocessor that acts as a central processing unit (CPU) for computer 14.

A memory 54 is accessible by processor 52, and may include program instructions that cause processor 52 to perform the functions attributed to processor 52 herein. Memory 54 may, for example, include communication program instructions 56 that cause processor 52 to wirelessly communicate medical event information with other medical devices as described herein, and run report generation or patient chart generation program instructions 58 that cause processor 52 generate a run report or patient chart, either automatically or in cooperation with a caregiver or administrator, based on at least some of the medical event information 60 stored in memory 54. Medical event information 60 stored in memory 54 may be received wirelessly from other medical devices, such as a defibrillator 12 or another computer 14, and may also include patient information received from a caregiver via a user interface 62. Memory 54 may include any of a variety of magnetic or optical media, such as RAM, ROM, CD-ROM, magnetic disk, or EEPROM.

User interface 62 may include input devices, such as a keyboard, keypad, pointing devices, or the like, and output devices, such as a CRT, LED or LCD display, speaker, or the like. In addition to receiving patient information from a caregiver via user interface, processor 52 may display medical event information 60 via user interface 62. Processor 52 may be responsive to commands received from a caregiver via user interface 62. In addition to receiving medical event information 60 from other medical devices, processor 52 may also be responsive to requests from other medical devices to provide medical event information 60 stored in memory 54 to the other medical devices.

In some embodiments, computer 14 may also include a network interface (not shown). Computer 14 may access a computer network, such as a computer network at a hospital, via the network interface. Caregivers may access medical event information 60 or a patient chart generated based on medical event information via the network.

Figure 4:
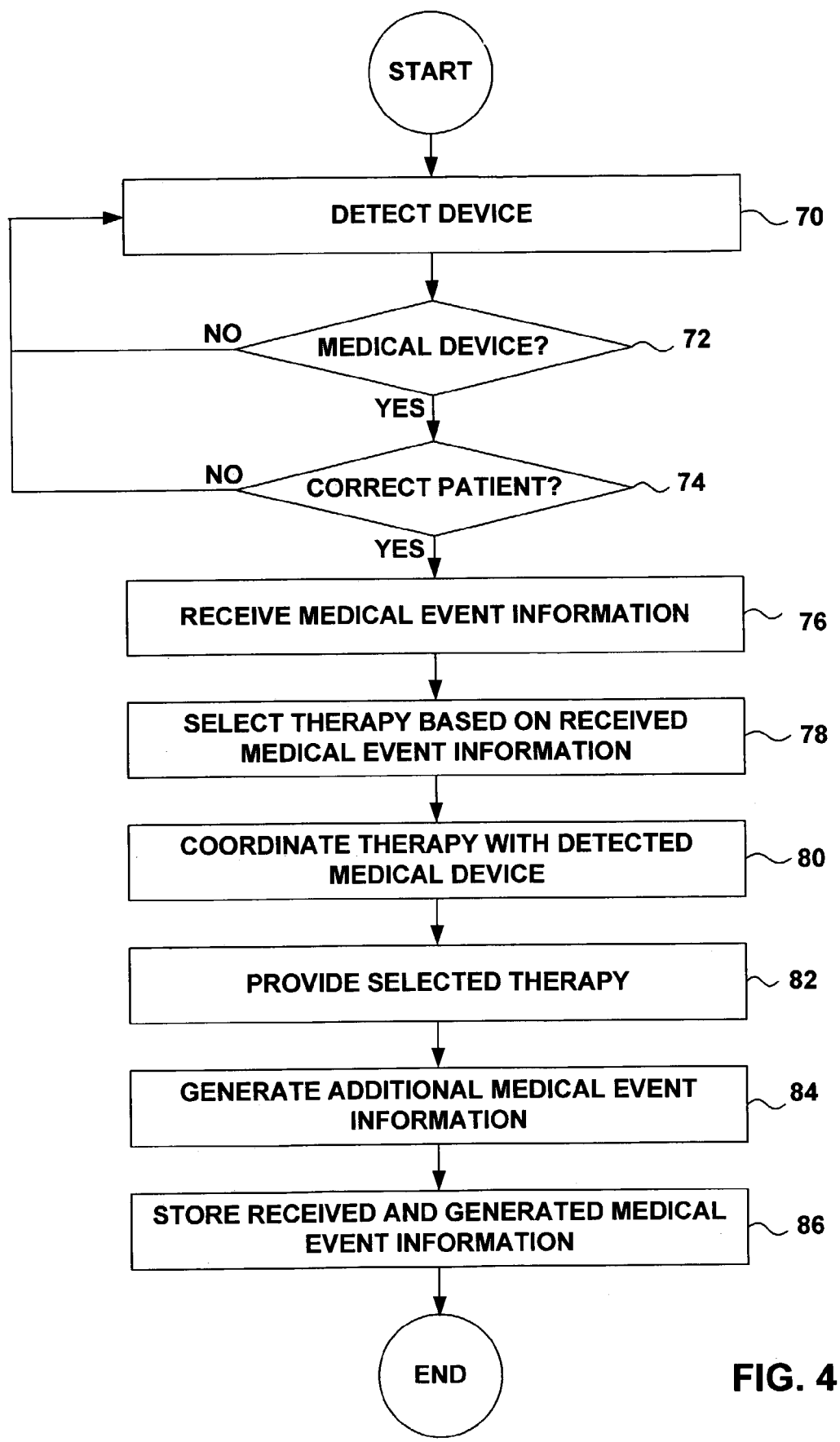
FIG. 4 is a flowchart illustrating an example method that may be employed by an external defibrillator to wirelessly receive medical event information from another medical device according to an embodiment of the invention.

FIG. 4 is a flowchart illustrating an example method that may be employed by an external defibrillator 12 to wirelessly receive medical event information from another medical device according to an embodiment of the invention. The method may, for example, be employed by a defibrillator 12 to receive medical event information from another defibrillator 12 or a computer 14. For ease of description, the method will be described with reference to the receipt of medical event information stored in defibrillator 12A by defibrillator 12B, which was previously discussed in reference FIG. 1.

When both defibrillator 12A and defibrillator 12B are turned on and proximate to each other such that wireless communication is possible, defibrillator 12B may detect defibrillator 12A via a wireless communication medium (70), and establish a local wireless communication session with defibrillator 12A in order to receive the medical event information stored in defibrillator 12A. The wireless communication medium may be a radio frequency (RF) communication medium, and defibrillator 12B may establish the local wireless communication session according to, for example, the Bluetooth or 802.11 specification sets.

Defibrillator 12B may establish the local wireless communication session by forming an ad hoc network with defibrillator 12A.

Defibrillator 12B may detect defibrillator 12A using an inquiry and response procedure. Defibrillator 12B may repeatedly broadcast messages via the local wireless communication medium. As illustrations, in the Bluetooth Specification, these messages are referred to as inquiry messages, while in the 802.11 specification, these messages are referred to as probe frames. Defibrillator 12B may, for example, begin to broadcast messages when turned on, or when directed by an associated caregiver.

If defibrillator 12A is turned on and within the communication range of defibrillator 12B, defibrillator 12A will receive an inquiry message, and may respond to the inquiry message with a response message that contains its address and other information needed by defibrillator 12B to establish a local wireless communications session with defibrillator 12A. Defibrillator 12B may then initiate the process of establishing the communication session, which may include negotiations between defibrillators 12A and 12B according to the protocol in use. Once these negotiations are complete, the communication session has been established and data packets may be transferred between defibrillators 12A and 12B.

In order to assure that it is receiving relevant medical event information, defibrillator 12B may additionally determine whether the defibrillator 12A is a medical device (72) and is associated with patient 16 (74). Defibrillator 12B may receive a device type indication from defibrillator 12A indicating that defibrillator 12A is a medical device. The device type indication may, for example, indicate that or defibrillator 12A is an external defibrillator, or may indicate that defibrillator 12A is an AED. Determining that defibrillator 12A is a medical device may allow defibrillator 12B to avoid establishing a communication session with other devices, such as cellular phones or non-medical wireless computing devices, located within its communication range and capable of local wireless communication according to the same standard.

Where defibrillator 12A is the only device detected by defibrillator 12B with a particular device type, defibrillator 12B may simply determine that defibrillator 12A is associated with patient 16 based on the detection of a single device of that type. Detection of multiple devices with the same device type is described in greater detail below. Defibrillator 12B may receive the device type indication from defibrillator 12A after the communication session has been established, during the negotiation of the communication session, or as part of the response message during the inquiry and response procedure.

Once the communication session is established, defibrillator 12B may receive the medical event information stored in defibrillator 12A (76). As mentioned above, the receipt of medical event information from defibrillator 12A may allow the caregiver associated with defibrillator 12B to provide patient 16 with more effective therapy. Defibrillator 12B or a caregiver associated with defibrillator 12B may select a therapy based on the received medical event information (78). For example, defibrillator 12B may use medical event information concerning the energy level of defibrillation pulses delivered by defibrillator 12A to select an energy level for a next defibrillation pulse to be delivered by defibrillator 12B, as described above.

Via the local wireless communication session, defibrillator 12B may coordinate the delivery of therapy to patient 16 with defibrillator 12A (80) by, for example, directing defibrillator 12A to cease delivering defibrillation pulses. Defibrillator 12B then delivers the selected therapy (82), e.g., a defibrillation pulse at the selected energy level.

During the treatment of patient 16, including the delivery of the selected therapy, defibrillator 12B, generates additional medical event information (84). The medical event information received from defibrillator 12A and the newly generated medical event information may be stored in a memory 24 (86).

Figure 5:
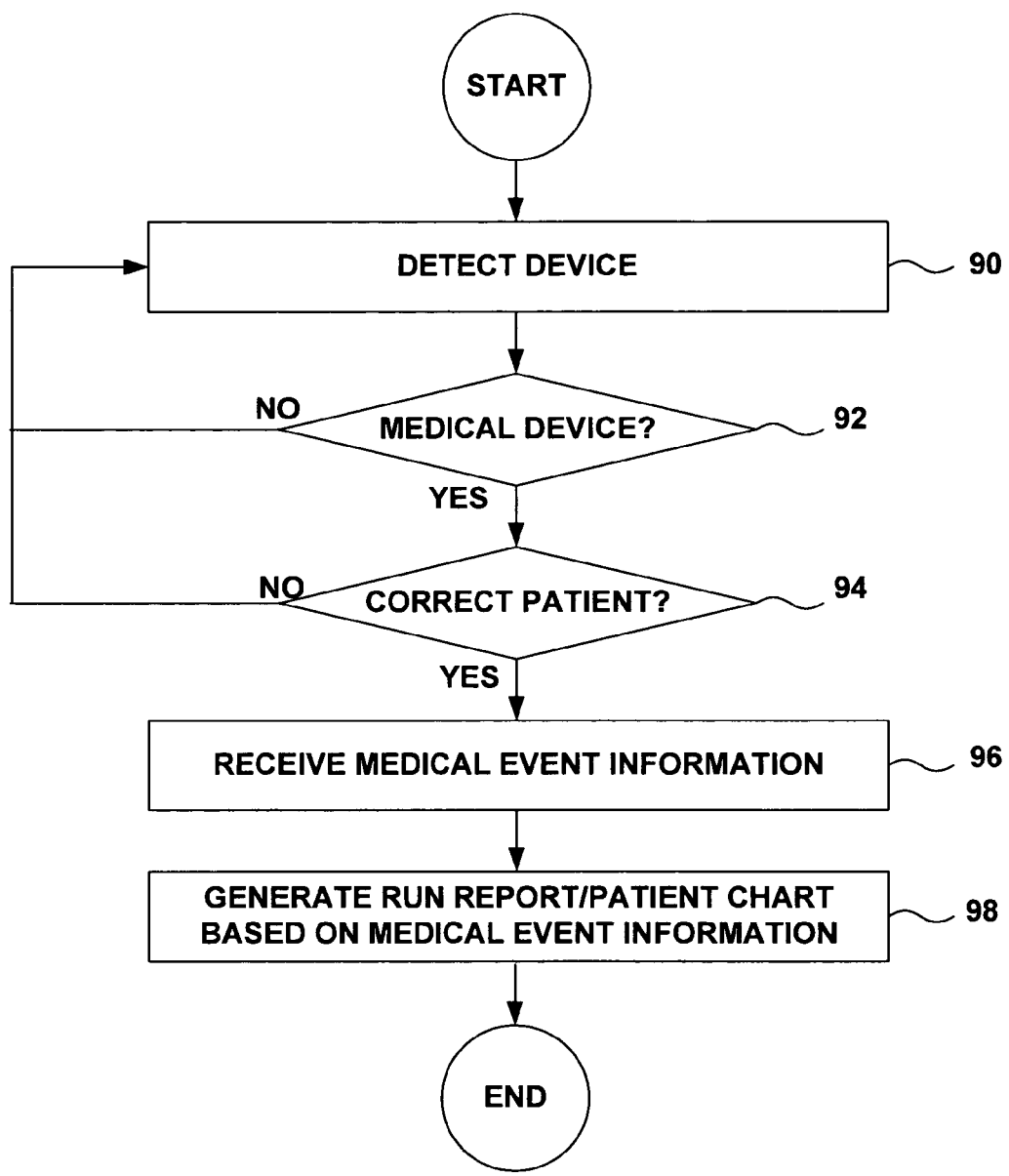
FIG. 5 is a flow chart illustrating an example method that may be employed by a computer to wirelessly receive medical event information from another medical device according to an embodiment of the invention.

FIG. 5 is a flow chart illustrating an example method that may be employed by a computer 14 to wirelessly receive medical event information from another medical device according to an embodiment of the invention. The method may, for example, be employed by a computer 14 to receive medical event information from a defibrillator 12 or another computer 14. For ease of description, the method will be described with reference to the receipt of medical event information stored in a defibrillator 12B by a computer 14, which was previously discussed with reference to FIG. 1.

Computer 14 may detect defibrillator 12B (90) and establish a local wireless communication session with defibrillator 12B, and receive the medical event information stored within defibrillator 12B in the manner that defibrillator 12B was described as performing these same functions in order to receive medical event information stored in defibrillator 12A with reference to FIG. 4. For example, computer 14 may detect defibrillator 12B using an inquiry and response procedure, and determine whether defibrillator 12B is a medical device (92) and associated with patient 16 (94), as described above. Upon receiving the medical event information stored in defibrillator 12B (96), which may include medical event information that defibrillator 12B wireless previously received from defibrillator 12A, computer 14 may generate a run report using at least some of the medical event information (98), as described above.

Figure 6:
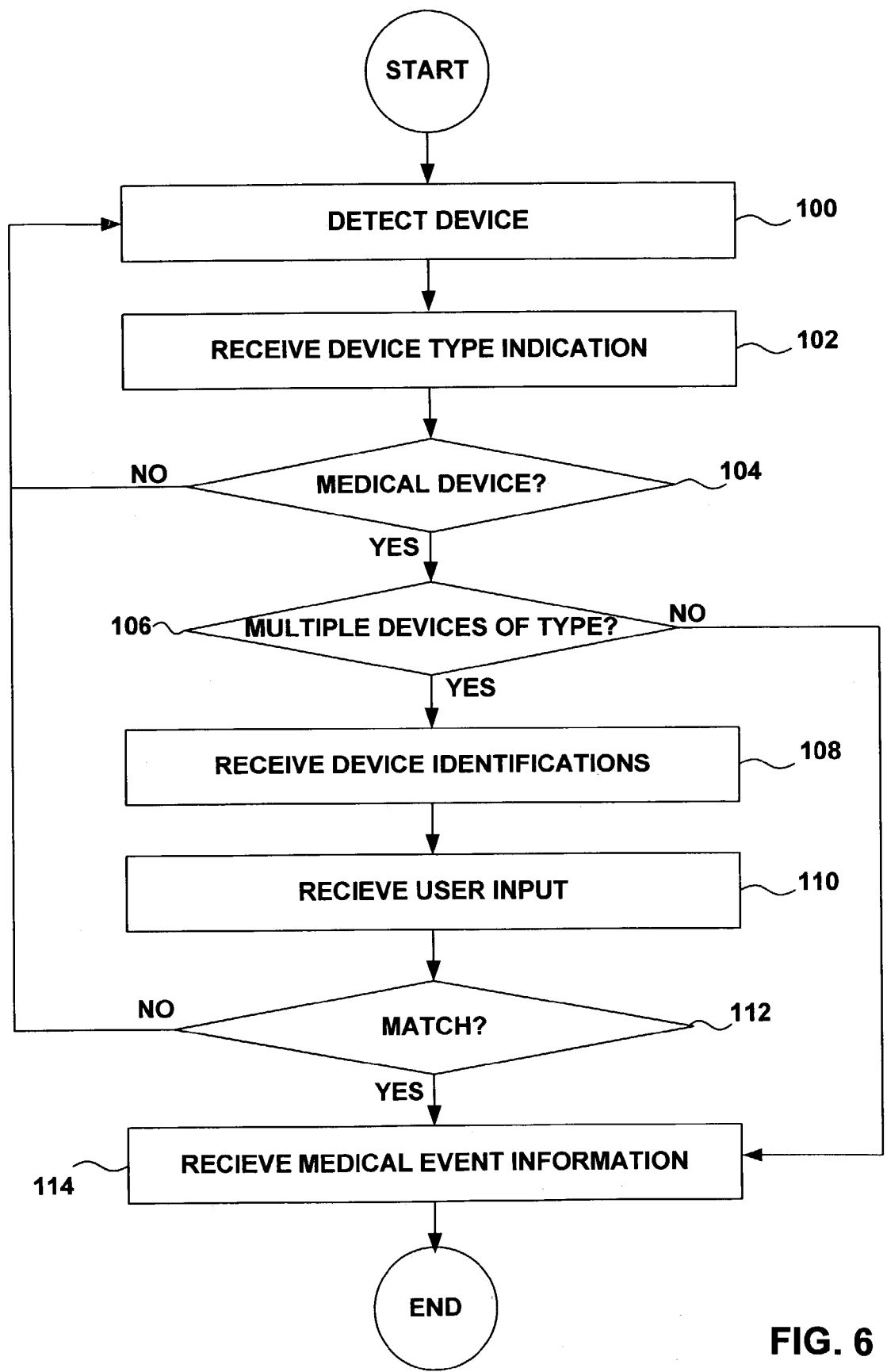
FIG. 6 is a flow chart illustrating an example method that may be employed by a medical device to receive medical event information from an appropriate one of a plurality of other medical devices according to an embodiment of the invention.

FIG. 6 is a flow chart illustrating an example method that may be employed by a medical device, such as a defibrillator 12 or computer 14, to receive medical event information from an appropriate one of a plurality of other medical devices of the same type, such as a plurality of defibrillators 12 or computers 14, according to an embodiment of the invention. Detecting an appropriate one of a plurality of medical devices may be particularly advantageous in situations where multiple defibrillators 12 and/or computers 14 are present for the treatment of multiple patients 16, such as the scene of a multiple vehicle accident, or within a hospital emergency department. For ease of description, the method will be described with reference to the receipt of medical event information stored in a defibrillator 12A by defibrillator 12B, which was previously discussed with reference to FIGS. 1 and 4.

Defibrillator 12B may detect defibrillator 12A (100), and receive a device type indication from defibrillator 12A in order to determine whether defibrillator 12A is a medical device (104), as described above. The device type indication received from defibrillator 12A may, for example, indicate that defibrillator 12A is an external defibrillator, or may indicate that defibrillator 12A is an AED. If defibrillator 12B does not detect any other devices of that device type, defibrillator 12B may determine that defibrillator 12A is associated with patient 16 based on the detection of a single device of that device type, as described above, and receive the medical event information stored in defibrillator 12A (114).

However, if defibrillator 12B detects multiple devices of the same device type, e.g., multiple external defibrillators or AEDs, defibrillator 12B may receive a device identification from each of the devices (108). Defibrillator 12B may determine that defibrillator 12A is associated with the appropriate patient 16 by comparing the received device identification to a device identification input by the caregiver using defibrillator 12B (110,112). The device identification for defibrillator 12A may be visible to the caregiver using defibrillator 12B on the exterior of defibrillator 12A, and defibrillator 12B may prompt the caregiver to enter the device identification via a user interface 42 of defibrillator 12B. Defibrillator 12B may receive one or both of the device type indication and the device identification after the communication session has been established, during the negotiation of the communication session, or as part of the response message during the inquiry and response procedure. If the device identification received from the caregiver matches the device identification received from defibrillator 12A, defibrillator 12B may receive the medical event information stored in defibrillator 12A (114).

Various embodiments of the invention have been described. These embodiments are illustrative of the practice of the invention. Various modifications may be made without departing from the scope of the claims. For example, paramedics may transmit the medical event information stored within a computer or defibrillator to hospital or emergency room in advance of their arrival to the hospital using cellular or landline phones, improving the ability of caregivers at hospital to timely assess the condition and treatment of a patient. The caregivers may be able to prepare for the arrival of the patient by, for example, preparing a catheterization lab or a thrombolytic treatment.

As another example, defibrillators may include or wirelessly communicate with a printer, allowing caregivers to print out received medical event information. This may allow the caregiver to quickly evaluate the condition and treatment of the patient prior to the patient being in their care. This may be particularly advantageous where paramedics take over the treatment of a patient from an inexperienced first responder that cannot provide adequate information concerning the condition or treatment of the patient.

As another example, a defibrillator or computer may be configured to communicate with an implanted medical device within a patient to receive historical patient condition and treatment information. This information may aid in the diagnosis and treatment of the patient in the field, and may be transported to a hospital with the patient.

Although medical devices have been described herein as external defibrillators or computers, the invention is not so limited. For example, various patient monitors, such as a patient respiration monitor, and therapy delivery devices, such as a drug delivery device, that participate in the monitoring and treatment of the patient may generate medical event information and wirelessly communicate the medical event information to other medical devices. These and other embodiments are within the scope of the following claims.

The invention claimed is:

1. A method comprising:
   detecting a device via a wireless communication medium;
   determining whether the detected device is a medical device and is associated with a patient;
   establishing a local wireless communication session with the device based on the determination;
   receiving medical event information from the detected device; and
   generating at least one of a run report or a patient chart based on the received medical event information,
   in which detecting a device includes performing a wireless inquiry and response procedure, and establishing a local wireless communication session comprises establishing an ad hoc wireless networking session with the detected device based on the procedure.

2. A method comprising:
   detecting a device via a wireless communication medium;
   determining whether the detected device is a medical device and is associated with a patient;
   establishing a local wireless communication session with the device based on the determination;
   receiving medical event information from the detected device; and
   generating at least one of a run report or a patient chart based on the received medical event information,
   in which determining whether the detected device is a medical device comprises receiving a device type indication from the detected device, and determining whether the detected device is associated with a patient comprises receiving a device identification from the detected device and comparing the device identification to a user input.

3. The method of claim 2, in which detecting the detected device comprises broadcasting messages and receiving a response to a broadcast message from the detected device via the wireless medium, and the response includes at least one of the device type indication and the device identification.

4. A method comprising:
   detecting a device via a wireless communication medium;
   determining whether the detected device is a medical device and is associated with a patient;
   establishing a local wireless communication session with the device based on the determination;
   receiving medical event information from the detected device;
   selecting a therapy to deliver to the patient based on the received medical event information;
   delivering the selected therapy to the patient;
   generating additional medical event information as a function of the delivery of the selected therapy; and
   storing the generated medical event information with the received medical event information,
   in which detecting the device comprises detecting a first medical device via a second medical device, selecting the therapy comprises selecting the therapy via the second medical device, and delivering the selected therapy comprises delivering the selected therapy via the second medical device.

5. A method comprising:
   detecting a device via a wireless communication medium;
   determining whether the detected device is a medical device and is associated with a patient; and
   establishing a local wireless communication session with the device based on the determination,
   wherein detecting the device comprises detecting a first medical device via a second medical device, the method further comprising:
   receiving medical event information from the first medical device via the local wireless communication session; and
   coordinating delivery of therapy to the patient by the first and second medical devices via the local wireless communication session,
   in which coordinating delivery of therapy to the patient comprises sending a message from the second medical device to the first device that directs the first device to suspend delivery of therapy.

6. A method comprising:
   detecting a device via a wireless communication medium;
   determining whether the detected device is a medical device and is associated with a patient;
   establishing a local wireless communication session with the device based on the determination;
   receiving medical event information from the detected device; and
   generating at least one of a run report or a patient chart based on the received medical event information, in which the detected device comprises a first medical device and the local wireless communication session comprises a first local wireless communication session, the method further comprising providing the received medical event information to at least one of a computing device or a second medical device via a second local wireless communication session with at least one of the computing device or the second medical device.

7. The method of claim 6, in which the second medical device is an external defibrillator.

8. A device comprising:
a transceiver to transmit and receive signals via a wireless medium; and
a processor to detect another device via the transceiver and the wireless medium, determine whether the detected device is a medical device and is associated with a patient, establish a local wireless communication session with the detected device based on the determination, receive medical event information from the detected device, and generate at least one of a run report or a patient chart based on the received medical event information.

9. The device of claim 8, in which the medical event information includes at least one of an electrocardiogram of the patient, a capnograph of the patient, a plethysmograph of the patient, a heart rate of the patient over time, a pulse rate of the patient over time, a blood oxygen saturation of the patient over time, a blood pressure of the patient over time, end tidal carbon dioxide measurements of the patient, measurements of the fraction of carbon dioxide in air inspired or expired by the patient, one or more therapies delivered to the patient, times at which the one or more therapies were delivered to the patient, or an audio recording.

10. The device of claim 8, in which the detected device is an external defibrillator.

11. The device of claim 8, in which the wireless medium is a radio frequency medium, and the wireless communication session is a radio frequency communication session.

12. The device of claim 8, in which the processor detects the device by performing a wireless inquiry and response procedure, and establishes a local wireless communication session with the detected device by establishing an ad hoc wireless networking session with the detected device based on the procedure.

13. The device of claim 8, further comprising a user interface, wherein the processor determines whether the detected device is a medical device by receiving a device type indication from the detected device via the transceiver, and determines whether the detected device is associated with a patient by receiving a device identification from the detected device via the transceiver and comparing the device identification to a user input received via the user interface.

14. The device of claim 13, in which the processor detects the device by broadcasting messages and receiving a response to a broadcast message from the device via the transceiver, and the response includes at least one of the device type indication and the device identification.

15. The device of claim 8, in which the processor sends medical event information to the detected device via the transceiver and the local wireless communication session.

16. The device of claim 8, in which the detected device comprises a first medical device and the local wireless communication session comprises a first local wireless communication session, and the processor provides the received medical event information to at least one of a computing device or a second medical device via a second local wireless communication session with at least one of the computing device or the second medical device.

17. The device of claim 16, in which the second medical device is an external defibrillator.

18. A device comprising:
a transceiver to transmit and receive signals via a wireless medium; and
a processor to detect another device via the transceiver and the wireless medium, determine whether the detected device is a medical device and is associated with a patient, establish a local wireless communication session with the detected device based on the determination, receive medical event information from the detected device, coordinate delivery of therapy to the patient with the detected device via the transceiver and the local wireless communication session by sending a message to the detected device via the transceiver and the local wireless communication session that directs the detected device to suspend delivery of therapy.

19. A computer-readable medium comprising instructions that cause a processor to:
detect a device via a wireless communications medium;
determine whether the detected device is a medical device and is associated with a patient;
establish a local wireless communication session with the detected device based on the determination;
receive medical event information from the detected device; and
generate at least one of a run report or a patient chart based on the received medical event information,
in which the instructions that cause a processor to detect a device comprise instructions that cause the processor to perform a wireless inquiry and response procedure, and the instructions that cause a processor to establish a local wireless communication session comprise instructions that cause the processor to establish an ad hoc wireless networking session with the detected device based on the procedure.

20. The computer-readable medium of claim 19, in which the instructions that cause a processor to determine whether the detected device is a medical device comprise instructions that cause a processor to receive a device type indication from the detected device, and the instructions that cause a processor to determine whether the detected device is associated with a patient comprise instructions that cause a processor to:
receive a device identification from the detected device; and
compare the device identification to a user input.

21. The computer-readable medium of claim 20, in which the instructions that cause a processor to detect the detected device comprise instructions that cause a processor to:
broadcast messages; and
receive a response to a broadcast message from the detected device, wherein the response includes at least one of the device type indication and the device identification.

22. The computer-readable medium of claim 19, further comprising instructions that cause a processor to send medical event information to the detected device.

23. The computer-readable medium of claim 19, in which the detected device comprises a first medical device and the local wireless communication session comprises a first local wireless communication session, the medium further comprising instructions that cause a processor to provide the received medical event information to at least one of a computing device or a second medical device via a second local wireless communication session with at least one of the computing device or the second medical device.

24. A computer-readable medium comprising instructions that cause a processor to:
   detect a device via a wireless communications medium;
   determine whether the detected device is a medical device and is associated with a patient;
   establish a local wireless communication session with the detected device based on the determination;
   receive medical event information from the detected device; and
   select a therapy for delivery to the patient based on the received medical event information;
   control delivery of the selected therapy to the patient;
   generate additional medical event information as a function of the delivery of the selected therapy; and
   store the generated medical event information with the received medical event information,
   in which the instructions that cause a processor to detect the device comprise instructions that cause a processor of a first medical device to detect a second medical device, the instructions that cause a processor to select the therapy comprises instructions that cause the processor of the first medical device to select the therapy, and the instructions that cause a processor to deliver the selected therapy comprise instructions that cause the processor of the first medical device to deliver the selected therapy.

25. A computer-readable medium comprising instructions that cause a processor to:
   detect a device via a wireless communications medium;
   determine whether the detected device is a medical device and is associated with a patient;
   establish a local wireless communication session with the detected device based on the determination; and
   receive medical event information from the detected device,
   wherein the instructions that cause a processor to detect the device comprises instructions that cause a processor of a first medical device to detect a second medical device,
   the medium further comprising instructions that cause the processor of the first medical device to coordinate the delivery of therapy to the patient by the first and second medical devices via the local wireless communication session, and
   in which the instructions that cause the processor of the first medical device to coordinate the delivery of therapy to the patient comprise instructions that cause the processor of the first medical device to send a message to the second medical device that directs the second medical device to suspend delivery of therapy.

26. A method comprising:
   receiving medical event information from a first medical device via a second medical device and a local wireless communication session between the first and second medical devices;
   selecting a therapy to deliver to a patient based on the medical event information via the second medical device; and
   delivering the selected therapy to the patient via the second medical device,
   in which receiving medical event information comprises the second medical device receiving the medical event information, selecting the therapy comprises the second medical device selecting the therapy, and delivering the selected therapy comprises the second medical device delivering the therapy.

27. The method of claim 26, in which the medical event information includes at least one of an electrocardiogram of the patient, a capnograph of the patient, a plethysmograph of the patient, a heart rate of the patient over time, a pulse rate of the patient overtime, a blood oxygen saturation of the patient over time, a blood pressure of the patient over time, end tidal carbon dioxide measurements of the patient, measurements of the fraction of carbon dioxide in air inspired or expired by the patient, one or more therapies delivered to the patient, times at which the one or more therapies were delivered to the patient, or an audio recording.

28. The method of claim 26, in which the first and second medical devices comprise external defibrillators.

29. The method of claim 26, in which the wireless medium is a radio frequency medium, and the wireless communication session is a radio frequency communication session.

30. A method comprising:
   receiving medical event information from a first medical device via a second medical device and a local wireless communication session between the first and second medical devices;
   selecting a therapy to deliver to a patient based on the medical event information via the second medical device;
   delivering the selected therapy to the patient via the second medical device; and
   coordinating delivery of therapy to the patient by the first and second medical devices via the local wireless communication session and the second medical device.

31. The method of claim 30, in which coordinating delivery of therapy to the patient comprises sending a message to the first device that directs the first device to suspend delivery of therapy, and the message is sent via the second device.

32. A device comprising:
   a transceiver to provide a local wireless communication session with a medical device;
   a circuit coupled to the patient; and
   a processor to receive medical event information from the medical device via the local wireless communication session and the transceiver, select a therapy to deliver to a patient based on the medical event information, deliver the therapy to the patient via the circuit, and coordinate delivery of therapy to the patient with the medical device via the local wireless communication session and the transceiver.

33. The device of claim 32, in which the processor sends a message to the medical device that directs the medical device to suspend delivery of therapy.

34. A computer-readable medium comprising instructions that cause a processor to:
   receive medical event information from a medical device via a local wireless communication session with the medical device;
   select a therapy to deliver to a patient based on the medical event information;
   deliver the selected therapy to the patient; and
   coordinate delivery of therapy to the patient with the medical device via the local wireless communication session.

35. The computer-readable medium of claim 34, in which the instructions that cause a processor to coordinate delivery of therapy to the patient comprise instructions that cause a processor to send a message to the medical device that directs the medical device to suspend delivery of therapy.

* * * * *

UNITED STATES PATENT AND TRADEMARK OFFICE
CERTIFICATE OF CORRECTION

PATENT NO. : 7,231,258 B2
APPLICATION NO. : 10/330808
DATED : June 12, 2007
INVENTOR(S) : Mark P. Moore et al.

It is certified that error appears in the above-identified patent and that said Letters Patent is hereby corrected as shown below:

In the drawings:
On Sheet 6 of 6, in FIG. 6 (Box No. 110), line 1, delete "RECIEVE" and insert -- RECEIVE --, therefor.

On Sheet 6 of 6, in FIG. 6 (Box No. 114), line 1, delete "RECIEVE" and insert -- RECEIVE --, therefor.

In column 7, line 53, delete "defibrillator. 12B" and insert -- defibrillator 12B --, therefor.

In column 9, line 26, delete "sets" and insert -- sets. --, therefor.

In column 14, line 2, delete "12B, generates" and insert -- 12B generates --, therefor.

In column 20, line 3, in Claim 27, delete "overtime," and insert -- over time, --, therefor.

Signed and Sealed this

Twenty-third Day of February, 2010

David J. Kappos
*Director of the United States Patent and Trademark Office*